United States Patent [19]

Lempriere

[11] Patent Number: 5,125,017
[45] Date of Patent: Jun. 23, 1992

[54] COMPTON BACKSCATTER GAGE

[75] Inventor: Brian M. Lempriere, Renton, Wash.

[73] Assignee: The United States of America as represented by the Secretary of the Air Force, Washington, D.C.

[21] Appl. No.: 648,457

[22] Filed: Jan. 30, 1991

[51] Int. Cl.⁵ .......................................... G01N 23/203
[52] U.S. Cl. ........................................ 378/86; 378/89;
378/145; 250/308
[58] Field of Search ................... 378/86, 87, 88, 89,
378/145, 147, 149; 250/308

[56] References Cited

U.S. PATENT DOCUMENTS

| 4,047,029 | 9/1977 | Allport | 250/273 |
| 4,258,256 | 3/1981 | Harding | 250/272 |
| 4,268,753 | 5/1981 | Murakami et al. | 378/86 |
| 4,277,686 | 7/1981 | Harding | 250/445 T |
| 4,582,993 | 4/1986 | Bhattacharya et al. | 250/359.1 |
| 4,688,240 | 8/1987 | Hosemann et al. | 378/70 |
| 4,825,454 | 4/1989 | Annis et al. | 378/86 |

FOREIGN PATENT DOCUMENTS

| 1146552 | 3/1985 | U.S.S.R. | 250/308 |
| 2055198 | 2/1981 | United Kingdom | 378/86 |

Primary Examiner—Janice A. Howell
Assistant Examiner—David P. Porta
Attorney, Agent, or Firm—William Stephanishen; Donald J. Singer

[57] ABSTRACT

A Compton x-ray backscatter gage apparatus directing x-rays from an isotopic radiation source to a region of interest in a composite structure to monitor structural integrity. The backscattered x-rays from the region of interest are directed by guides in the gage housing to radiation detectors.

11 Claims, 1 Drawing Sheet

COMPTON BACKSCATTER GAGE

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to a non-destructive structure monitoring sensor and, more particularly, to a Compton backscatter gage apparatus to monitor the structural degradation of composite materials.

The state of the art of backscatter gage apparatus is well represented and alleviated to some degree by the prior art apparatus and approaches which are contained in the following U.S. Patents:

U.S. Pat. No. 4,688,240 issued to Hosemann et al on Aug. 18, 1987;

U.S. Pat. No. 4,582,993 issued to Bhattacharya et al on Apr. 15, 1986;

U.S. Pat. No. 4,277,686 issued to Harding on Jul. 7, 1981;

U.S. Pat. No. 4,258,256 issued to Harding on Mar. 24, 1981; and

U.S. Pat. No. 4,047,029 issued to Allport on Sept. 6, 1977.

The Hosemann et al patent discloses a method for non-destructive testing of structural material. Diffraction scattering and oriented reflection of x-rays at the individual atoms and lattice planes in the crystalline structure are used to determine the integrity of the compound material. X-ray sensitive film or detectors such as scintillation counters are used to determine reflection patterns. Any change in deposition and configuration of the dispersed x-ray over time is indicative of internal tension or stress of the material under test.

The Bhattacharya et al patent discloses a method and apparatus for detecting voids in or on the surface of cast metal. A collimated beam of photons is passed through the cast metal, and the photon flux emerging is detected. The presence of a void in the cast metal will result in an increase in the photon flux received by the photon detector, and a subsequent increase in the output signal.

The Harding '686 patent discloses a device for measuring a scatter coefficient distribution in a plane of a body. The plane is irradiated, and the scattered radiation which is generated is measured by detectors, which enclose the body as completely as possible.

The Harding '256 patent describes a device which detects scattered radiation and reduces the measurement disturbance caused by multiple scatter radiation. Flat laminations are arranged between the primary beam in a fan of flat planes. The flat laminations transmit scattered radiation, which originates in the region of the primary beam, to the detectors, and attenuate scattered radiation, which originates outside of the primary beam.

The Allport patent discloses a gage for determining properties (thickness/density), of sheet material by measuring the attenuation and backscatter of radiant energy, which is directed on the material under test. The gage consists of a pair of radiation detectors. One detector measures the energy attenuation, while the other measures the energy backscatter. Each detector generates electrical signals proportional to the detected energy levels. A computer utilizes this data to determine the desired material properties.

Space structures made of composite materials, and some airborne and earth-bound structures as well, will require constant monitoring to determine the state of their structural health, because of the degradation they suffer in the severe environments in which they operate and the importance of adequate warning of any impending failure.

This monitoring will require non-destructive sensors which can examine critical parts of the structure to determine any sources of incipient failure, such as growing cracks. The subject of health monitoring for composites is new, and has not as yet led to useful techniques, but the possibility of using x-rays for inspection always arises. The conventional concept of bulky x-ray inspection equipment, however, is not adaptable to multiple remote operation in space.

Recently, backscattered x-rays are being exploited as a means of producing one-sided inspection in a variety of applications, frequently, however, these imitate the existing x-ray applications of digital radiography or computer tomography and are even more bulky than simple x-ray techniques. This disclosure presents a concept for using backscattered x-rays on a small scale.

While the above-cited references are instructive, there still remains a need to provide an apparatus which constantly monitors the structural state of the composite materials in severe environments. The present invention is intended to satisfy that need.

SUMMARY OF THE INVENTION

The present invention utilizes a Compton backscatter gage to constantly monitor the structural health of composite materials used in airborne and earth bound structures, and to warn of impending failure. The apparatus contains a small passive x-ray source, radiation detector(s), and a mounting which provides collimation and shielding. The detectors measure the average backscattered x-rays from a small portion of the material. The gage continually provides an electrical output, which may be integrated over time, and is a measure of the average backscatter. The backscatter intensity depends on the electronic density of the material. Any changes in the backscatter signal represent material density or chemistry changes, which may be caused by a phenomena such as a crack in the material.

It is one object of the invention to provide an improved Compton backscatter gage apparatus.

It is one object of the invention to provide an improved Compton backscatter gage apparatus that provides passive non-destructive structural monitoring of composite materials.

It is still another object of the invention to provide an improved Compton backscatter gage apparatus that measures the degradation of composite structures in severe and in accessible environments.

It is yet another object of the invention to provide an improved Compton backscatter gage apparatus which can inspect specific critical parts of a structure to determine any sources of incipient failure.

These and other advantages, objects and features of the invention will become more apparent after considering the following description taken in conjunction with the illustrative embodiment in the accompanying drawings.

DESCRIPTION OF THE PREFERRED EMBODIMENT

Figure 1:
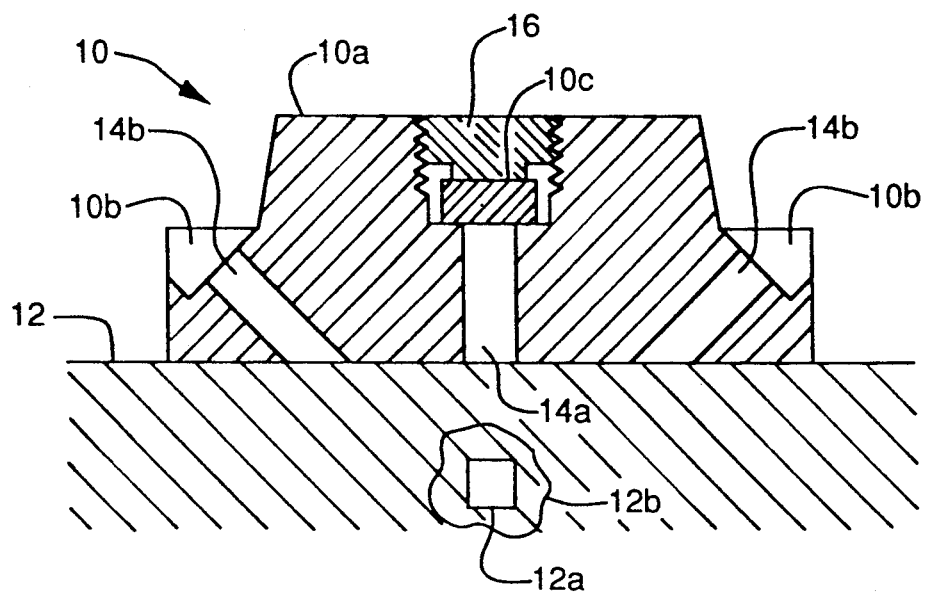
FIG. 1 is a cross-sectional view of the Compton backscatter gage apparatus according to the present invention.

Referring now to FIG. 1, there is shown a cross-sectional view of the Compton backscatter gage 10 which is mounted on structure 12. The Compton backscatter gage 10 comprises a housing and collimating shield 10a, a ring detector 10b and an isotopic x-ray source 10c. The housing and collimating shield 10a includes a radiation guide 14a and backscatter guides 14b. A set screw 16 or other suitable conventional means is utilized to hold the x-ray source 10c in place. The radiation guide 14a directs the emitted x-rays from the isotopic x-ray source 10c to the inspection volume 12a within the structure 12. The inspection volume 12a is located within the region of interest 12b in the structure 12. The backscattered radiation from the inspection volume 12a are directed by the backscatter guides 14b to the ring detector 10b.

Figure 2:
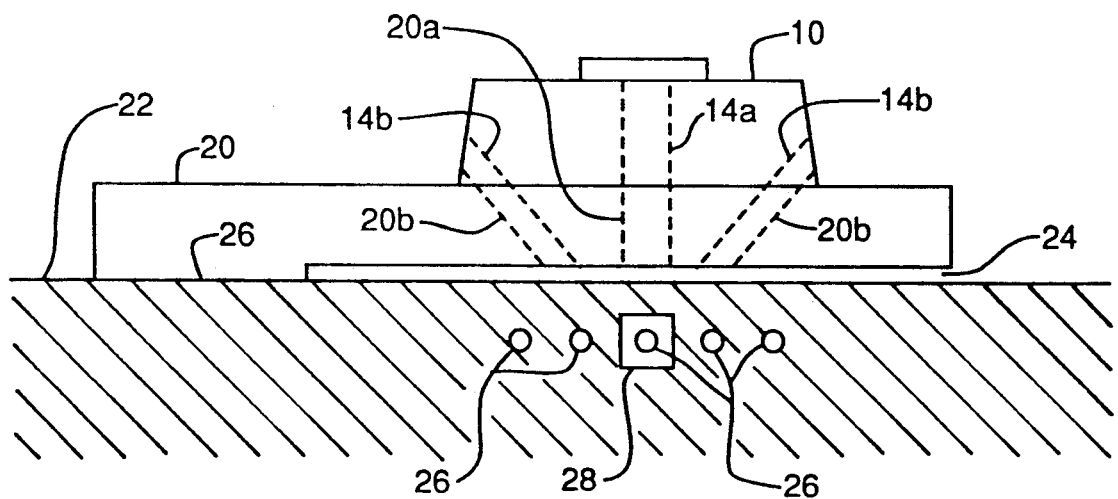
FIG. 2 is a schematic diagram of the Compton backscatter gage apparatus utilized in a strain gage application.

Turning now to FIG. 2, there is shown a schematic representation of the Compton backscatter gage in a strain gage application. A backscatter gage 10 of the type shown and described in FIG. 1 is mounted by any suitable commercially available means to the top surface of an L-shaped housing 20. Direct and backscatter guides 20a, 20b are provided in the L-shaped housing in alignment with the corresponding guides 14a, 14b in the backscatter gage 10. The L-shaped housing 20 comprises a high density material to confine the direct and backscatter radiation to the guides 20a, 20b and thereby reduce or eliminate signal losses. The one end 26 of the L-shaped housing 20 is bonded to the surface of the composite structure 22. The other end of the L-shaped structure in the vicinity of the backscatter gage 10 is raised above the surface of structure 22 to provide a small air gap or spaces therebetween. The air gap 24 allows relative motion to occur between the L-shaped structure 20 and the composite structure 22. Beneath the surface of composite structure 22 and in the vicinity of the intersection 28 of the direct and backscatter guides 20a, 20b there are wires 26 embedded in the composite structure 22. The wires 26 will be monitored by the backscatter gage 10 to determine any strains or deformities that occur in the composite structure 22. The embedded wires 26 may all be comprised of the same material or each wire may be comprised of various different materials or elements.

When one specific feature of a structure is to be inspected continuously, backscattered x-rays can be used in a small easily applied and remotely monitored device akin to a gage. The preferred embodiment of the apparatus is illustrated in different applications in FIGS. 1 and 2. It comprises a small passive x-radiation source of a radioactive isotope, one or more small radiation detectors, and a housing structure which provides collimation and shielding. The radiation detector may be either passive or active, in which case a power source for the detector may be needed. If needed, signal conditioning for the output, such as a local amplifier and integrator, may also be utilized. The basic form illustrated is an application in which a local effect such as a crack is to be monitored. Another application as a motion sensor, such as a strain gage, uses an embedded grid of wires of various elements. In order to improve the signal-to-noise ratio in slowly changing situations, the x-ray backscatter apparatus may be provided with a small jitter motion by mounting it on flexible arm with a piezo-electric film actuator.

The needed strength of the isotopic x-ray source will depend on the rate of inspection required of the application, but in most cases can be as small as a medicine pill, provided several seconds of data gathering are acceptable and the material under inspection is not too thick or dense. The detector may be a simple gas-filled tube or a photosensitive device, and can be mounted in photon collector such as a polymeric ring. It may require a low power source, though perhaps at high voltage, and provides a current output indicative of the photon count, and therefore of the intensity of the received backscatter.

In operation, the gage continuously provides an electrical output which is integrated over periods of time sufficient to separate signal from noise. The integrated signal, a measure of the average backscatter from a small portion of the material defined by the collimation, is then used as an indicator of health through its relationship to whatever material parameter is under observation. Essentially the backscatter intensity depends on the electronic density or the material in the observation volume, so that changes of signal represent changes of material density or chemistry.

Although the invention has been described with reference to a particular embodiment, it will be understood to those skilled in the art that the invention is capable of a variety of alternative embodiments within the spirit and scope of the appended claims.

What is claimed is:

1. A compton backscatter apparatus comprising in combination:

a housing containing a radiation guide and a predetermined number of backscatter guides to form a backscatter gage, said backscatter gage including a chamber within its upper portion which is aligned substantially in the center of said housing, said radiation guide operatively communicating with said chamber and extending perpendicularly therefrom to the lower surface of said housing, said backscatter guides are spaced around the periphery of said housing and are positioned at an acute angle with respect to said radiation guide, said backscatter guides each respectively communicating with a detector unit at its upper end, said backscatter guides extending through said housing to the lower surface thereof;

an x-ray source operatively positioned within said chamber to emit x-rays into said radiation guide; and a structure which is monitored to determine its structural condition, said backscatter gage positioned on said structure so that the intersection of said radiation guide and said backscatter guides defines a region of interest within said structure, x-rays from said x-ray radiation source are focused upon said region of interest and are then backscatter to said detector units, said compton backscatter apparatus and further including an L-shaped member which is bonded at one end to said structure and at the other end provides a gap therebetween to allow relative motion between said member and said structure, said backscatter gage positioned upon said L-shaped member in the region of said gap, said L-shaped member including collimating guides corresponding to and aligned with said radiation guide and backscatter guides of said backscatter gage, said structure including embedded wires at the intersection of said radiation guide and said backscatter guides.

2. A Compton backscatter apparatus as described in claim 1 wherein said x-ray source comprises a passive x-radiation source.

3. A Compton backscatter apparatus as described in claim 1 wherein said housing comprises a high density material to provide a collimating shield for said x-rays.

4. A Compton backscatter apparatus as described in claim 1 wherein said predetermined number of backscatter guides comprise two.

5. A Compton backscatter apparatus as described in claim 1 wherein said x-ray source comprises a radioactive isotope pellet.

6. A Compton backscatter apparatus as described in claim 1 wherein said detector unit comprises a gas-filled tube.

7. A Compton backscatter apparatus as described in claim 1 wherein said detector unit comprises a photosensitive device.

8. A Compton backscatter apparatus as described in claim 1 wherein said structure comprises a composite material.

9. A Compton backscatter apparatus as described in claim 8 wherein said L-shaped member comprises a high density material.

10. A Compton backscatter apparatus as described in claim 8 wherein said embedded wires comprise the same material.

11. A Compton backscatter apparatus as described in claim 10 wherein said embedded wires comprise different materials.

* * * * *